US010359532B2

(12) United States Patent
Jain et al.

(10) Patent No.: US 10,359,532 B2
(45) Date of Patent: Jul. 23, 2019

(54) METHODS TO CHARACTERIZE FORMATION PROPERTIES

(71) Applicant: Schlumberger Technology Corporation, Sugar Land, TX (US)

(72) Inventors: Vikas Jain, Sugar Land, TX (US); Kais Gzara, Tunis (TN)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 522 days.

(21) Appl. No.: 14/957,481

(22) Filed: Dec. 2, 2015

(65) Prior Publication Data

US 2016/0170065 A1 Jun. 16, 2016

Related U.S. Application Data

(60) Provisional application No. 62/090,231, filed on Dec. 10, 2014.

(51) Int. Cl.
*G01V 1/42* (2006.01)
*G01V 3/14* (2006.01)
(Continued)

(52) U.S. Cl.
CPC ............ *G01V 3/14* (2013.01); *G01V 3/38* (2013.01); *G01N 24/081* (2013.01);
(Continued)

(58) Field of Classification Search
CPC .. G01V 3/14–38; G01N 24/08; G01N 24/081; G01R 33/448–4641; G01R 33/48–586
(Continued)

(56) References Cited

U.S. PATENT DOCUMENTS 5,381,092 A 1/1995 Freedman
5,991,236 A 11/1999 Yamamoto
(Continued)

FOREIGN PATENT DOCUMENTS

WO 2010039757 A1 4/2010

OTHER PUBLICATIONS

Drori; Fast I1 Minimization by Iterative Thresholding for Multidimensional NMR Spectroscopy; Pub. Date Aug. 28, 2007; EURASIP Journal Advances in Signal Processing; vol. 2007, Article ID 20248; p. 1-10.*

(Continued)

*Primary Examiner* — Melissa J Koval
*Assistant Examiner* — Rahul Maini

(57) ABSTRACT

A method for analyzing at least one characteristic of a geological formation may include obtaining measured data for the geological formation based upon a logging tool. Measured data may come from multiple passes or multiple depths of investigation. The method may further include generating a kernel describing a known linear mapping between the measured data and unknown data points representing at least one characteristic of the geological formation, and a redundant dictionary including a plurality of different basis functions expected to span the solution space of the unknown data points. The unknown data points representing the at least one characteristic of the geological formation may be determined from the measured data, the kernel and the redundant dictionary based upon an L1 minimization.

23 Claims, 6 Drawing Sheets

(51) Int. Cl.
  *G01V 3/24* (2006.01)
  *G01V 3/30* (2006.01)
  *G01V 3/38* (2006.01)
  *G01N 24/08* (2006.01)
  *G01R 33/44* (2006.01)
  *G01R 33/46* (2006.01)

(52) U.S. Cl.
  CPC ........ *G01R 33/448* (2013.01); *G01R 33/4633* (2013.01); *G01V 1/42* (2013.01); *G01V 3/24* (2013.01); *G01V 3/30* (2013.01)

(58) Field of Classification Search
  USPC ....................................................... 324/303
  See application file for complete search history.

(56) References Cited

U.S. PATENT DOCUMENTS

| | | | |
|---|---|---|---|
| 6,060,884 A | 5/2000 | Meyer, Jr. et al. | |
| 6,374,201 B1 | 4/2002 | Grizon et al. | |
| 6,750,864 B1* | 6/2004 | Anwar | G06F 17/30489 345/440 |
| 8,259,531 B2* | 9/2012 | Lie | G01V 1/364 367/51 |
| 8,600,115 B2* | 12/2013 | Liu | G01V 3/38 324/324 |
| 2003/0229449 A1 | 12/2003 | Merchant et al. | |
| 2004/0145370 A1 | 7/2004 | Conti | |
| 2004/0169511 A1 | 9/2004 | Minh et al. | |
| 2005/0104587 A1 | 5/2005 | Akkurt | |
| 2006/0055403 A1* | 3/2006 | Freedman | G01V 1/44 324/303 |
| 2008/0183425 A1 | 7/2008 | Hines | |
| 2009/0010558 A1* | 1/2009 | Dekel | G06F 17/30247 382/248 |
| 2009/0093961 A1 | 4/2009 | Valero et al. | |
| 2009/0259406 A1 | 10/2009 | Khadhraoui et al. | |
| 2010/0010744 A1* | 1/2010 | Prange | G01V 3/32 324/303 |
| 2010/0026294 A1 | 2/2010 | Lustig et al. | |
| 2010/0138157 A1* | 6/2010 | Sun | G01V 3/32 702/6 |
| 2010/0271019 A1 | 10/2010 | Anand et al. | |
| 2011/0262041 A1* | 10/2011 | Bharath | G06K 9/4671 382/190 |
| 2011/0313737 A1 | 12/2011 | Hadj-Sassi et al. | |
| 2012/0026314 A1 | 2/2012 | Zhdanov | |
| 2012/0065888 A1 | 3/2012 | Wu et al. | |
| 2012/0143506 A1 | 6/2012 | Routh et al. | |
| 2012/0209528 A1 | 8/2012 | Itskovich | |
| 2013/0085730 A1 | 4/2013 | Shaw et al. | |
| 2013/0214779 A1 | 8/2013 | Tietjen et al. | |
| 2013/0325353 A1* | 12/2013 | Otvos | G01R 33/465 702/19 |
| 2014/0005945 A1 | 1/2014 | Anand et al. | |
| 2014/0122037 A1 | 5/2014 | Prange et al. | |
| 2014/0129149 A1 | 5/2014 | Gzara et al. | |
| 2014/0214324 A1 | 7/2014 | Freedman et al. | |
| 2014/0358897 A1* | 12/2014 | Mishra | G06F 17/3087 707/722 |
| 2015/0110381 A1* | 4/2015 | Parvin | G06K 9/6249 382/133 |
| 2016/0054467 A1 | 2/2016 | Li et al. | |
| 2016/0146973 A1* | 5/2016 | Johnson | G01V 1/306 702/2 |

OTHER PUBLICATIONS

Antoniadis; Wavelet methods in statistics: Some recent developments and their applications; Dec. 3, 2007; vol. 1 [2007] 16-55; p. 40.*
Papgerogiou et al. ("Sparse Correlation Kernel Analysis and Reconstruction"; May 1998; Massachusetts Institute of Technology Artificial Intelligence Laboratory; A.I. Memo No. 1635, C.B.C.L Paper No. 162; p. 1-25).*
Written Opinion issued in the related PCT application PCT application PCT/US2015/063638 dated Mar. 29, 2016 (7 pages).
International Preliminary Report on Patentability issued in the related PCT application PCT/US2015/046707 dated Feb. 28, 2017 (5 pages).
International Preliminary Report on Patentability issued in the related PCT application PCT/US2015/063638 dated Jun. 13, 2017 (8 pages).
Allen et al., "How to Use Borehole Nuclear Magnetic Resonance," Oilfield Review, Summer 1997: pp. 34-57.
International Search Report issued in related PCT application PCT/US2015/046707 dated Nov. 30, 2015, 3 pages.
Written Opinion issued in related PCT application PCT/US2015/046707 dated Nov. 30, 2015, 4 pages.
International Search Report issued in related PCT application PCT/US2015/063638 dated Mar. 29, 2016, 3 pages.
Final Office Action issued in U.S. Appl. No. 14/470,052 dated Feb. 8, 2018. 13 pages.

* cited by examiner

METHODS TO CHARACTERIZE FORMATION PROPERTIES

CROSS-REFERENCE TO RELATED APPLICATIONS

The present application claims priority to U.S. Provisional Application Ser. No. 62/090,231 filed Dec. 10, 2014, the entirety of which is incorporated by reference.

FIELD OF THE INVENTION

Aspects relate to downhole drilling. More specifically, aspects relate to determination of formation property characteristics.

BACKGROUND

Logging tools may be used in wellbores to make, for example, formation evaluation measurements to infer properties of the formations surrounding the borehole and the fluids in the formations. Common logging tools include electromagnetic tools, acoustic tools, nuclear tools, and nuclear magnetic resonance (NMR) tools, though various other tool types are also used.

Early logging tools were run into a wellbore on a wireline cable, after the wellbore had been drilled. Modern versions of such wireline tools are still used extensively. However, the desire for real-time or near real-time information while drilling the borehole gave rise to measurement-while-drilling (MWD) tools and logging-while-drilling (LWD) tools. By collecting and processing such information during the drilling process, the driller may modify or enhance well operations to optimize drilling performance and/or well trajectory.

MWD tools generally provide drilling parameter information such as weight-on-bit, torque, shock & vibration, temperature, pressure, rotations-per-minute (rpm), mud flow rate, direction, and inclination. LWD tools generally provide formation evaluation measurements such as natural or spectral gamma-ray, resistivity, dielectric, sonic velocity, density, photoelectric factor, neutron porosity, sigma thermal neutron capture cross-section, a variety of neutron induced gamma-ray spectra, and NMR distributions. MWD and LWD tools often have components common to wireline tools (e.g., transmitting and receiving antennas or sensors in general), but MWD and LWD tools may be constructed to endure and operate in the harsh environment of drilling. The terms MWD and LWD are often used interchangeably, and the use of either term in this disclosure will be understood to include both the collection of formation and wellbore information, as well as data on movement and placement of the drilling assembly.

Logging tools may be used to determine formation volumetrics, that is, quantify the volumetric fraction, generally expressed as a percentage, of each constituent present in a given sample of formation under study. Formation volumetrics involves the identification of the constituents present, and the assigning of unique signatures for constituents on different log measurements. When, using a corresponding earth model, the forward model responses of the individual constituents are calibrated, the log measurements may be converted to volumetric fractions of constituents.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method for analyzing at least one characteristic of a geological formation may include obtaining measured data for the geological formation based upon a logging tool. Measured data may come from multiple passes or multiple depths of investigation. The method may further include generating a kernel describing a known linear mapping between the measured data and unknown data points representing at least one characteristic of the geological formation, and a redundant dictionary including a plurality of different basis functions expected to span the solution space of the unknown data points. The unknown data points representing the at least one characteristic of the geological formation may be determined from the measured data, the kernel and the redundant dictionary based upon an L1 minimization.

A related apparatus for analyzing at least one characteristic of a geological formation may include a memory and a processor cooperating therewith to obtain measured data for the geological formation based upon a logging tool. Measured data may come from multiple passes or multiple depths of investigation. The processor may further generate a kernel describing a known linear mapping between the measured data and unknown data points representing at least one characteristic of the geological formation, and a redundant dictionary including a plurality of different basis functions expected to span the solution space of the unknown data points. The processor may also determine the unknown data points representing the at least one characteristic of the geological formation from the measured data, the kernel and the redundant dictionary based upon an L1 minimization.

A related non-transitory computer-readable medium may have computer-executable instructions for causing a computer to at least obtain measured data for the geological formation based upon a logging tool, generate a kernel describing a known linear mapping between the measured data and unknown data points representing at least one characteristic of the geological formation, and generate a redundant dictionary including a plurality of different basis functions expected to span the solution space of the unknown data points. Measured data may come from multiple passes or multiple depths of investigation. The unknown data points representing the at least one characteristic of the geological formation may be determined from the measured data, the kernel and the redundant dictionary based upon an L1 minimization.

DETAILED DESCRIPTION

The present description is made with reference to the accompanying drawings, in which example embodiments are shown. However, many different embodiments may be used, and thus the description should not be construed as limited to the embodiments set forth herein. Rather, these embodiments are provided so that this disclosure will be thorough and complete. Like numbers refer to like elements throughout.

Generally speaking, the present disclosure relates to an approach for inversion of downhole or laboratory measurements, such as multi-dimensional NMR measurements, to predict accurate formation characteristics. The method minimizes the norm of the inversion parameters to reduce the artifacts that are often present in typical inversion results obtained by existing approaches.

Figure 1:
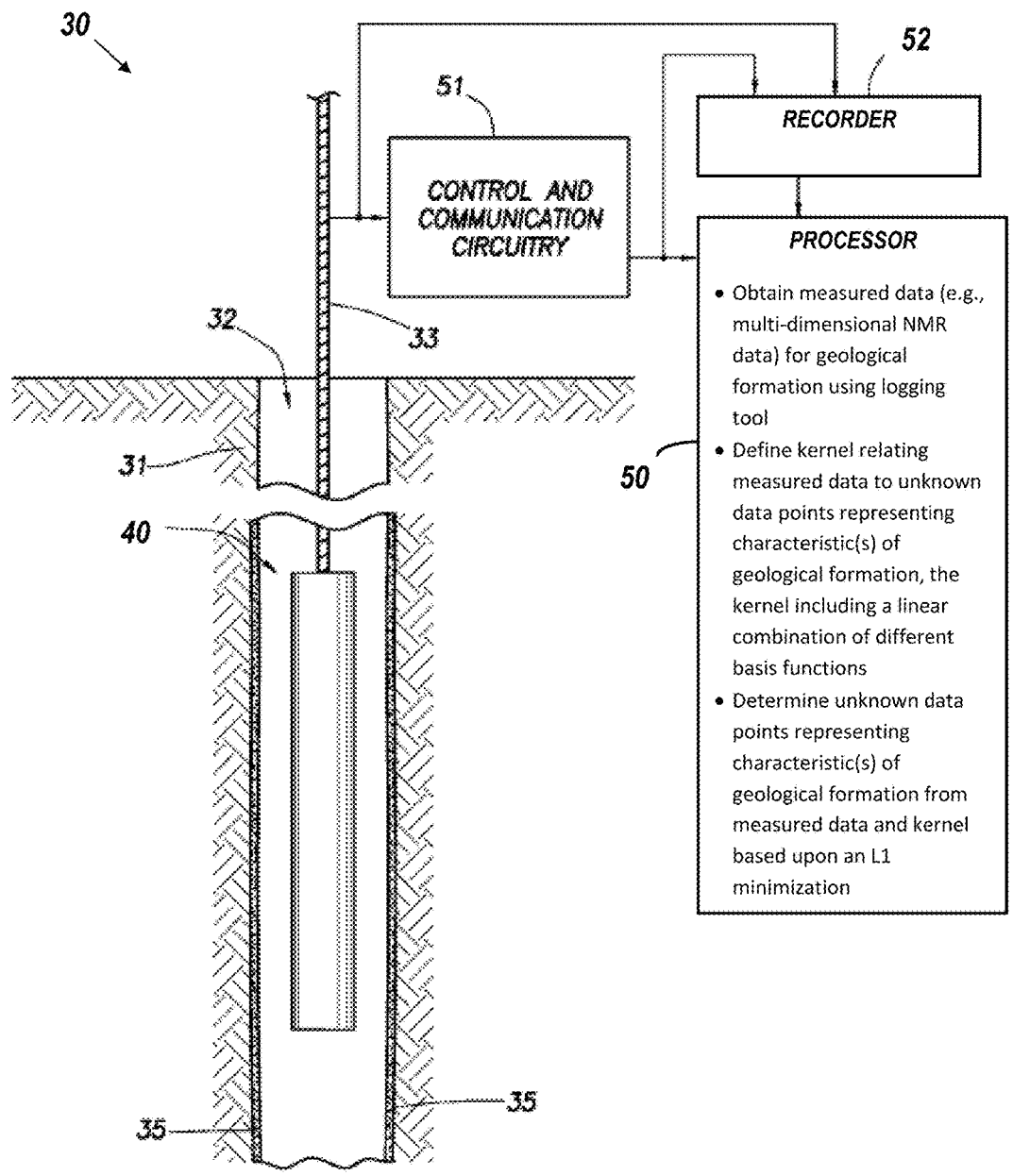
FIG. 1 is a schematic diagram, partially in block form, of a well logging apparatus which may be used for determining characteristics of formation properties in accordance with an example embodiment.
Figure 2:
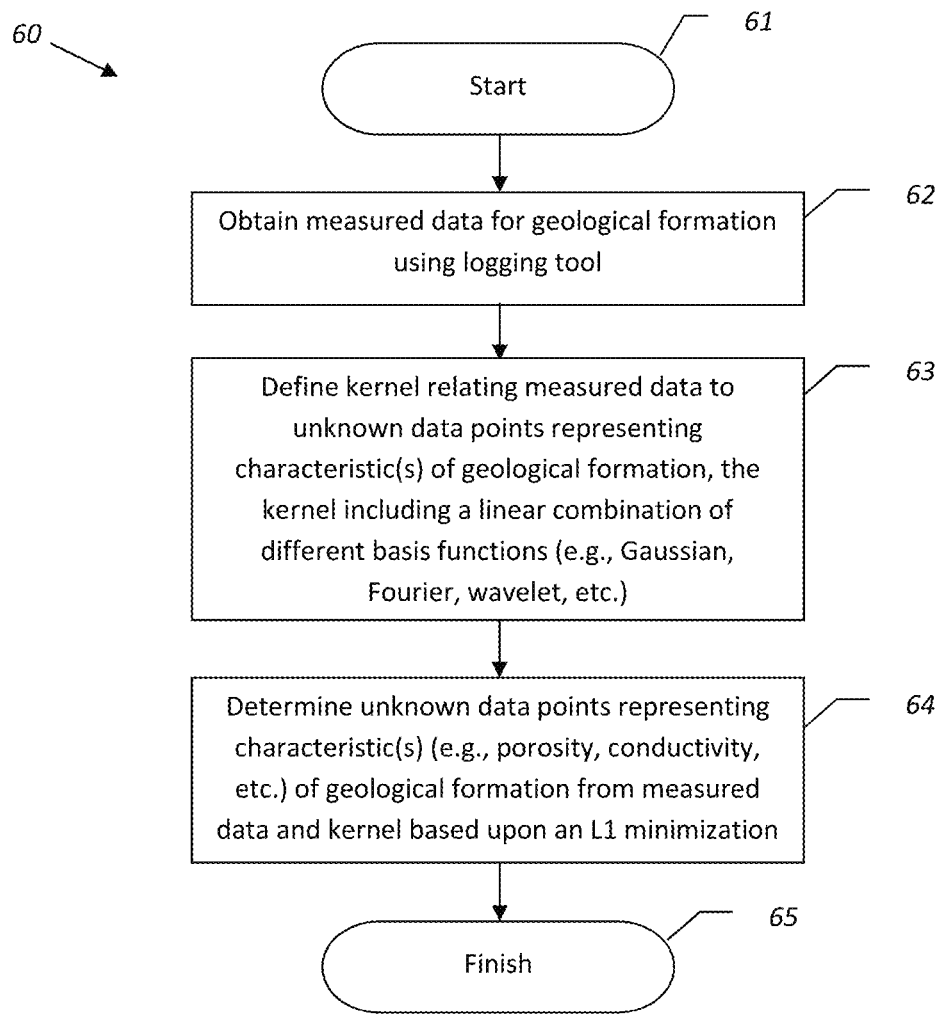
FIG. 2 is a flow diagram illustrating method aspects for determining characteristics of formation properties in accordance with an example embodiment.

Referring initially to FIG. 1 and the flow diagram 60 of FIG. 2, an example well logging system 30 and associated method aspects are first described. Beginning at Block 61, the system 30 may be used for taking measurements (e.g., multi-dimensional nuclear magnetic resonance (NMR) data measurements) for use in determining characteristics of formation properties, such as porosity distribution, etc., in accordance with the approach described further below (Block 62). However, it should be noted that the data may be obtained in other ways, such as through surface measurements, measurements of geological samples taken in a laboratory setting, etc., in addition to borehole measurements, and with other types of logging tools, as will be appreciated by those skilled in the art.

More particularly, a borehole 32 is drilled in a formation 31 with drilling equipment, and may use drilling fluid or mud. One or more portions of the borehole 32 may be lined with a casing 35, which may include metal (e.g., steel) cylindrical tubing, coiled tubing, cement, or a combination thereof. Other configurations may include: non-metallic casings such as fiberglass, high strength plastic, nano-material reinforced plastics, etc.; screens as used in some completions to prevent or reduce sanding; and slotted liners that may be used in completion of horizontal wells, for example. A logging device or tool 40 is suspended in the borehole 32 on an armored multiconductor cable 33 to provide a wireline configuration, although other configurations such as logging while drilling (LWD), measurement while drilling (MWD), Slickline, coiled tubing or configurations such as logging while tripping may also be used. The length of the cable 33 substantially determines the depth of the device 40 within the borehole 32. A depth gauge apparatus may be provided to measure cable displacement over a sheave wheel (not shown), and thus the depth of logging device 40 in the borehole 32.

Control and communication circuitry 51 is shown at the surface of the formation 31, although portions thereof may be downhole. Also, a recorder 52 is also illustratively included for recording well-logging data, as well as a processor 50 for processing the data. However, one or both of the recorder 52 and processor 50 may be remotely located from the well site. The processor 50 may be implemented using one or more computing devices with appropriate hardware (e.g., microprocessor, memory, etc.) and non-transitory computer-readable medium components having computer-readable instructions for performing the various operations described herein. It should also be noted that the recorder 52 may also be located in the tool, as may be the case in LWD tools, which may send a subset of data to the surface while storing the bulk of the data in memory downhole to be read out at the surface after tripping out of the hole. In Slickline implementations there may be no communication with the surface, and data will be recorded and may be processed downhole for later retrieval and potentially further processing at the surface or a remote location.

The tool 40 may include one or more types of logging devices that take measurements from which formation characteristics may be determined. For example, the logging device may be an electrical type of logging device (including devices such as resistivity, induction, and electromagnetic propagation devices), a nuclear logging device (e.g., NMR), a sonic logging device, or a fluid sampling logging device, as well as combinations of these and other devices, as will be discussed further below. Devices may be combined in a tool string and/or used during separate logging runs. Also, measurements may be taken during drilling, tripping, and/or sliding. Some examples of the types of formation characteristics that may be determined using these types of devices include the following: determination, from deep three-dimensional electromagnetic measurements, of distance and direction to faults or deposits such as salt domes or hydrocarbons; determination, from acoustic shear and/or compressional wave speeds and/or wave attenuations, of formation porosity, permeability, and/or lithology; determination of formation anisotropy from electromagnetic and/or acoustic measurements; determination, from attenuation and frequency of a rod or plate vibrating in a fluid, of formation fluid viscosity and/or density; determination, from resistivity and/or nuclear magnetic resonance (NMR) measurements, of formation water saturation and/or permeability; determination, from count rates of gamma rays and/or neutrons at spaced detectors, of formation porosity and/or density; and determination, from electromagnetic, acoustic and/or nuclear measurements, of formation bed thickness.

By way of background, the estimation of formation properties, such as porosity distribution, from downhole or laboratory measurements generally involves the solution of inverse problems. The conventional method of solution of inverse problem involves L2 minimization of the penalty function which is generally of the form of the sum of squared formation properties (i.e. L2 norm) subject to the constraints that the sum of squared differences or error between the measurements and a theoretical model relating the measurements and formation properties (i.e., L2 norm) should be within some acceptable bounds and that the value of any of the formation properties should not be negative. The theoretical model can be linear or non-linear, and is obtained theoretically or empirically.

More particularly, petrophysical systems which take the form M=KQ, where it is desired to invert for quantities Q of interest using acquired measurements M and a known kernel K, are non-trivial. This is because mostly the system is ill-posed, rank deficient and ill-conditioned. Moreover, right hand side singular eigenvectors of K do not necessarily and effectively span the complete solution space of Q. This creates undesirable features and artifacts on the inverted solution Q using conventional method of using L2 minimization as described above.

This is particularly evident in NMR inversions of the form E=KF, when attempting to invert single to multi-dimensional distribution F. F is generally a 1D T2 distribution, 2D T1-T2 distribution, 2D D-T2 distribution, 3D D-T1-T2 distribution, or it may be an even higher dimensional. The problems noted above become more even pronounced in a higher dimensional solution space of F. Also, NMR-acquired data is equi-sampled in time, creating density of data in T2 sub-space. However data density is sparse in other dimensions. This results in poor sensitivity to individual components in those dimensions (e.g., D, T1, etc.).

Generally speaking, to circumvent these problems, the embodiments set forth herein may employ additional information related to the nature and characteristics of the solution space of the formation properties, which are added to the original problem as a pre-condition. For NMR, the solution space of F is spanned by Gaussians. Thus, a redundant dictionary including a set of Gaussians may be used to pre-condition F in the form of F=GA, where G is the redundant dictionary of the Gaussians and A is a vector of corresponding amplitudes. By the nature of both F and G, it is known that a very few amplitudes in A are going to be non-zero or that A is going to be highly sparse. To ensure this known sparsity in A, a modified penalty term including the sum of the absolute values of the amplitudes in A (i.e., the L1 norm) should be minimized (called L1 minimization) subject to the same constraints as described previously. F is reconstructed after inverting for A using the redundant dictionary of Gaussians. Inverted distributions have good resolution in dimensions where data sampling is poor. This is due to the cumulative nature of signals in those dimensions. Inversion using the "redundant" dictionaries and L1 minimization as described herein may be extended to various linear or non-linear systems representing sub-surface or petrophysical data acquisitions.

More particularly, most often petrophysical systems take the following form:

$$M=KQ \quad (1)$$

Where M=is an m*1 vectorized collection of single or multi-dimensional measurements acquired over each depth sample, Q=is a q*1 vectorized collection of single or multi-dimensional variables that we are interested in solving (e.g., porosity distribution, fluid volumes, acoustic slowness or other petrophysical quantities of interest), and K=is an m*q kernel relating M to V through known or empirical relationships. If Q is known, then it is straightforward to forward model M using equation (1) above.

However, the inverse problem, using acquired M to solve for desired Q, is non-trivial. There may be several reasons for this. First, equation (1) is ill-posed, in that the system is underdetermined. This results in non-unique or infinitely many solutions. Furthermore, the kernel K is rank deficient in both row and column space. Rank deficiency in row space leads to an under-determined system, even if a multitude of measurements or measurement samples are acquired. Basically, there are few independent measurements or measurement samples which may be utilized. Column rank deficiency leads to sub-optimal coverage of the solution space of Q. Thus, the solution space of Q is covered preferentially, creating unwanted artifacts/features in inverted Q. Still another reason for the non-trivial nature of the inverse problem is that the kernel K is generally ill-conditioned because of rank deficiency. This means that a small perturbation or noise on the acquired measurements M will lead to a potentially massive change in Q. This necessitates use of regularization to keep change in check.

Because of above reasons, Q is generally inverted using minimization of cost and penalty functions as described below:

Cost Function: $\quad \|M - K\hat{Q}\|_c \quad (2)$
(where $c$ is normally 2 or $L2$ norm)

Penalty Function: $\quad \lambda\|\hat{Q}\|_p \quad (3a)$
(where $p$ is normally 2 or $L2$ norm)

Minimization Function: $\quad \min_{\hat{Q}}(\|\hat{Q}\|_p) \text{ s.t. } \|M - K\hat{Q}\|_c \le \epsilon \quad (3b)$ Equivalent quadratic formulation: $\quad \min_{\hat{Q}}(\|M - K\hat{Q}\|_c + \lambda\|\hat{Q}\|_p) \quad (4)$ The sum of the cost and penalty functions is minimized over the possible values of Q. Being a convex function, equation (4) may be solved using a number of solvers available for convex optimization. The quality of the solution Q is generally found to be highly dependent on the choice of λ. This is to be expected since K is highly ill-conditioned. Since elements of Q represent petrophysical and/or real world quantities, they are non-negative. Thus, minimization is done with a positivity constraint on each element of Q. Elements of Q can be further bounded to improve solution quality. Non-negativity and bounded nature of the solution space also acts as added regularization.

In some situations, Q may be sparse. For example, this may be the case for NMR inversion in 2D or higher. Sparsity is defined as the fraction of non-zero elements over the total number of elements in Q. In these cases, the traditionally used L2 penalty function has a drawback in that it is adverse to sparsity. L2 minimization tends to try to fit Q to M using K by forcing most elements of Q to be non-zero. If the nature of the solution space Q is known to be sparse, or if that space may be transformed to a sparse space, then L1 minimization may be used as the penalty function to help ensure sparsity. L1 minimization tries to balance minimization of L0 or support as well as L2. This forces most elements of solution to be 0 and thus, sparse. This type of minimization may result in better and more robust solutions, as will be appreciated by those skilled in the art.

To reduce reliance on λ and to improve the quality of answer Q, the present approach solves equation (1) above in two steps using a priori information about the nature of Q. More particularly, using a suitable set or dictionary of basis functions for Q allows Q to be written as a linear combination of these basis functions. Even if the exact nature of Q or its basis functions are unknown, a standard set of basis functions may be used, such as wavelets or Fourier basis functions or series, for example. In this regard, let B represent a set or dictionary of basis functions. Then, $$Q = BA \quad (5)$$

The original equation (1) may be re-formulated as:

$$M = (KB)A \quad (6)$$

There are a number of advantages that may be gained from this re-formulation. First, new kernel KB is generally found to be better conditioned, reducing reliance on regularization. Furthermore, using basis functions in the combined kernel KB may better span the solution space of Q. Additionally, B is a dictionary of basis functions of the solution space, but the solution Q itself is generally going to be a linear combination of relatively few of these basis functions. This essentially means that A is going to be sparse and have relatively few non-zero elements compared to Q. Thus, we can use better penalty norms, such as L1, to solve equation (6).

Accordingly, a new kernel and minimization functions may be defined as follows:

Transformed Kernel: $K' = KB$ (7)

Penalty Function: $\lambda \|\hat{A}\|_1$ (8a)

Minimization Function: $\min_{\hat{Q}}(\|\hat{Q}\|_1) \text{ s.t. } \|M - K\hat{Q}\|_2 \leq \epsilon$ (8b)

Equivalent quadratic formulation: $\min_{\hat{A}}(\|M - K'\hat{A}\|_2 + \lambda \|\hat{A}\|_1)$ (9)

Solution: $\hat{Q} = B\hat{A}$ (10)

Using L1 minimization may help ensure sparsity in $\hat{A}$. $\hat{Q}$ is reconstructed using inverted $\hat{A}$ and desired basis functions in B. This helps ensure that $\hat{Q}$ may indeed be anywhere in the entire solution space and is no longer dependent on the preferential basis functions of the original kernel K.

The foregoing will now be applied to an example implementation using the above described combination of solution dictionary and L1 minimization to perform a 2D inversion of NMR data. For this purpose, NMR echoes were simulated for a number of cases. White noise was added to the echoes to reflect real data acquisition. Inversion was performed for amplitudes at each allowed (T1, T2) pair. A (T1, T2) pair is allowed if it lies within certain prescribed limits on the T1/T2 ratio. So, the problem to be solved may be re-written as:

NMR Example: $E = KF$ (11)

E is acquired echoes using preconfigured acquisition Carr-Purcell-Meiboom-Gill (CPMG) sequence. A typical length of E in downhole applications may generally be between 600 and 6000. F is a distribution of amplitudes as a function f(T1, T2). Depending on a minimum and maximum T1/T2 ratio, a typical number of such (T1, T2) pairs may be around 270, which then is also the dimension of vectorized F. The maximum dimension of F is the number of T1 components*number of T2 components, assuming no constraint on T1/T2 ratios. K is the kernel relating E to F. The dimension of K is length(E)*length(F). $K_{ij}$ is:

$$K_{ij} = \left[(1[e^{-WT_k/T1_j})e^{i_k \frac{TE_k}{T2_j}}\right]\sqrt{NR_k} \quad (12)$$

where k represents the $k^{th}$ CPMG sequence in a complete NMR echo acquisition.

The system of equations in equation (11) represents a linear system and is equivalent to the system in equation (1), meaning that it also suffers from the same problems. Traditionally (11) is solved using the following minimization function:

$$\text{NMR Minimization Function: } \min_{\hat{F}}(\|E' - K\hat{F}\|_2 + \lambda \|\hat{F}\|_2) \quad (13)$$

where E' represents the standardized echoes against noise (square root of number of repeats) for each sub-measurement. Similarly, λ is a sum of regularization parameters for each sub-measurement weighted by squared noise or number of repeats.

If relatively few sub-measurements with few wait times are present, then it is generally understood that there will not be sufficient sensitivity to T1 and thus, 1D inversion alone is performed for T2. A typical case will use 3 sub-measurements with wait times of 16, 48 and 13,000 ms, for example. This is equivalent to sampling the T1 space at 3 points. Attempting a 2D inversion for such a case using minimization as shown in equation (13) demonstrates that the inverted amplitudes will have little to no sensitivity to T1.

Figure 3:
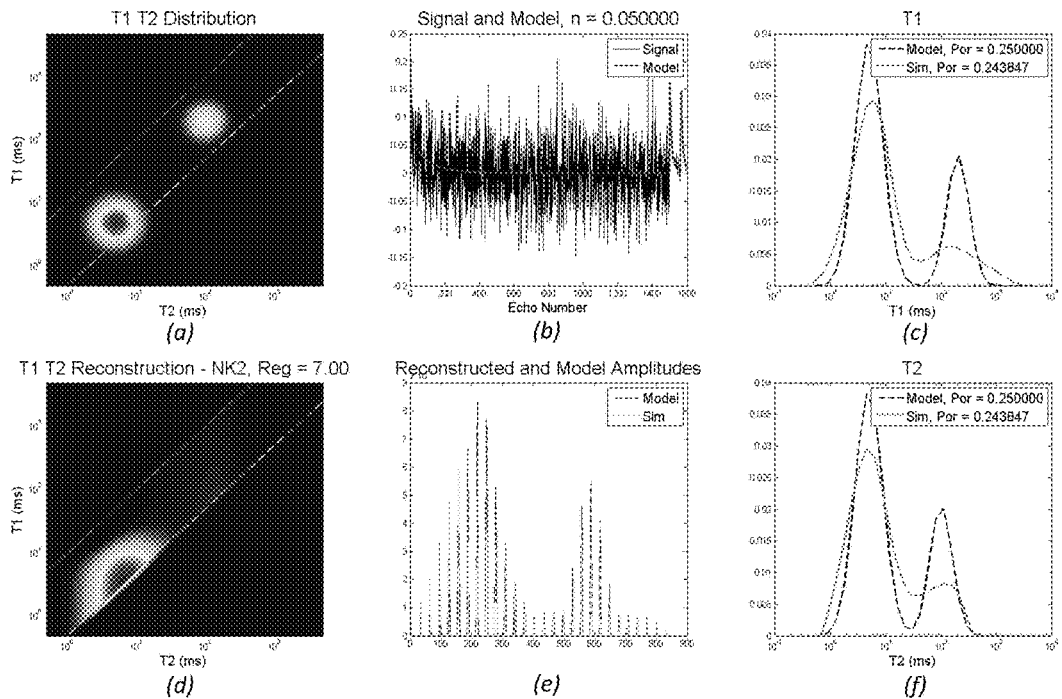
FIG. 3 is a set of graphs illustrating T1-T2 inversion results using L2 norm minimization for a first example data set in accordance with a conventional approach.

This may be seen in FIG. 3, in which T1-T2 inversion results are provided for a first example using a non-negative least square L2 penalty minimization. In FIG. 3, the top left graph (a) is the model T1-T2 distribution, the top middle graph (b) is simulated noiseless and noisy echoes, the top right graph (c) is a projected T1 distribution (model in dashed and inverted in solid lines), the bottom left graph (d) is the inverted T1-T2 distribution, the bottom middle graph (e) is the vectorized model T1-T2 distribution (dashed) and inverted version (solid), and the bottom right graph (f) is the projected T2 distribution (model in dashed and inverted in solid). Note that in FIGS. 4-8, the graphs (a)-(f) are set out in the same fashion as in FIG. 3 (just for different minimization functions or data sets), so the above description of what each graph (a)-(f) represents will not be repeated for each of FIGS. 4-8 below.

Figure 5:
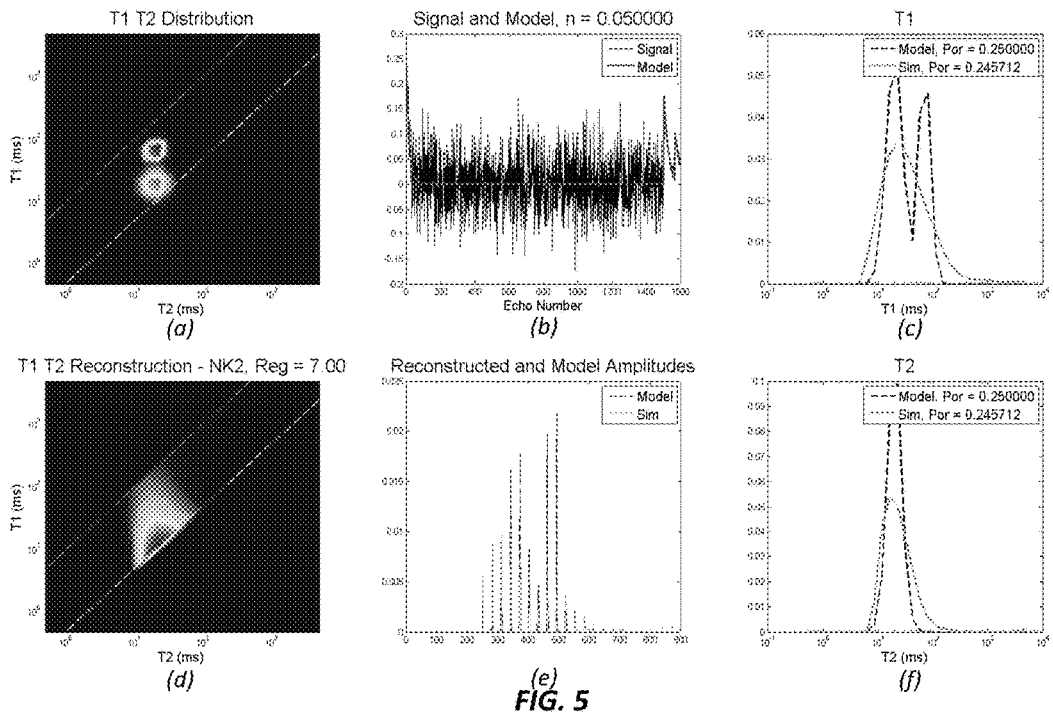
FIG. 5 is a set of graphs illustrating T1-T2 inversion results using L2 norm minimization for a second example data set in accordance with a conventional approach.

In the example of FIG. 5, a second example data set is used, and similar T1-T2 inversion results using non-negative least square L2 penalty minimization is observed. FIGS. 3 and 5 accordingly highlight how inadequate the L2 inversion may be in resolving T1 components of F. A typical approach to overcome this inadequacy is to increase the number of sub-measurements and, in turn, the number of wait times to have better sampling of T1 space. Yet, there are difficulties with this approach. First, it may be difficult to determine how many wait times are sufficient for desired T1 resolution. Secondly, this increases the time it will take to acquire measurements at each depth level downhole. Increasing measurement time is not generally accepted in an industry where time is at a premium while drilling.

Equation (11) was accordingly reformulated using the same mechanics as set forth in equations (5) and (6). For this purpose, basis functions of F were chosen to be Gaussians of different widths. To ensure that the Gaussians are weighted equally in this example, the height of each was adjusted to be the same. Thus, a redundant dictionary of Gaussians of the same amplitude was created with widths from a set of standard deviations centered on the allowed (T1, T2) pairs. In a typical implementation, there may be thirty T1 components and thirty T2 components with around 270 allowed (T1, T2) pairs. Assuming a set of five standard deviations, a dictionary of Gaussians will be of dimension (30*30)*(270*5), or 900*1350. Such a dictionary will be orthogonal, and the potential F will have a support of no more than 7-10 Gaussians. So, the problem cast in this manner will be highly sparse. In accordance with one example, a sparsity of less than 10/1350 was achieved, i.e., less than 1%.

Equation (13) may accordingly be reformulated as:

| | | |
|---|---|---|
| Using dictionary of Gaussians: | $F = GA$ (Where $G$ is the dictionary of Gaussians of the same amplitude and standard deviation from the set of 5.) | (14) |
| Recasting original problem: | $E = K'A; K' = KG$ (Here $A$ is highly sparse creating an opportunity to use $L1$ minimization) | (15) |
| Modified NMR Minimization Function: | $\min_{\hat{F}} \left( \left\| E' - K'\hat{A} \right\|_2 + \lambda \|\hat{A}\|_1 \right)$ ($E'$ is standarized echoes against noise in each sub-measurement. Penalty function is now an $L1$ norm.) | (16) |
| Reconstruction of $F$: | $\hat{F} = G\hat{A}$ | (17) |

Figure 4:
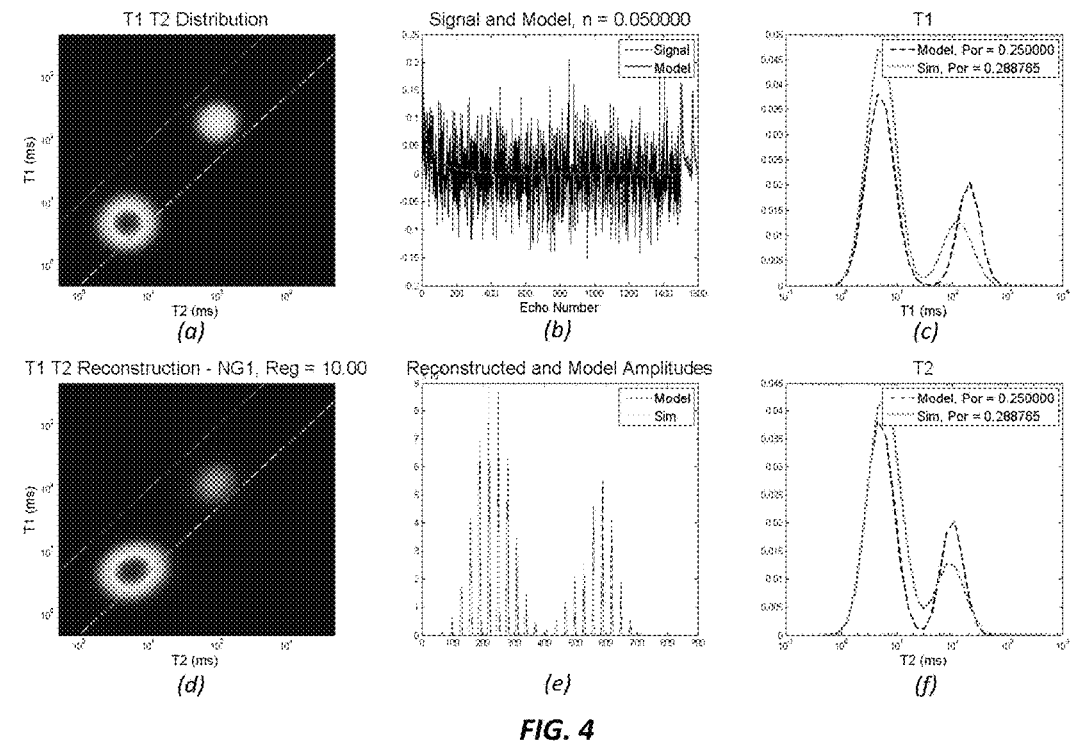
FIG. 4 is a set of graphs illustrating T1-T2 inversion results using a redundant dictionary of Gaussians and L1 norm minimization for the first example data set in accordance with an example embodiment.
Figure 6:
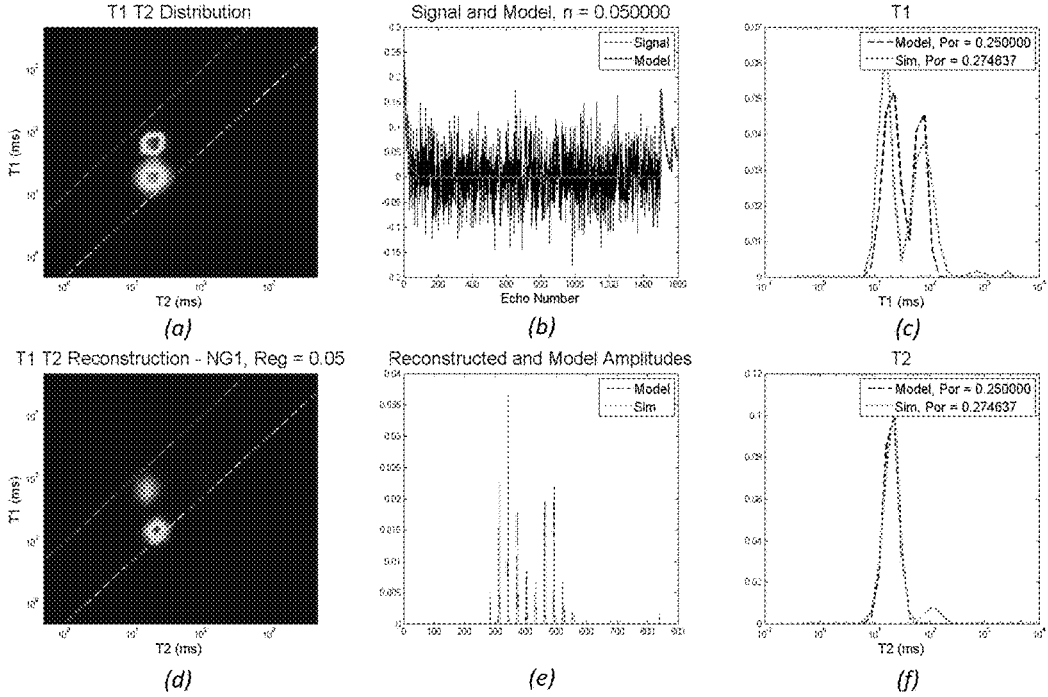
FIG. 6 is a set of graphs illustrating T1-T2 inversion results using a redundant dictionary of Gaussians and L1 norm minimization for the second example data set in accordance with an example embodiment.

Using convex optimization algorithms, L1 minimization may be performed to solve for $\hat{A}$. $\hat{A}$ will have relatively few non-zero elements, which is desirable. $\hat{F}$ may then be reconstructed from $\hat{A}$ using equation (17). The first and second example data sets noted above were again processed, but this time using the dictionary and L1 minimization approach set forth in equations (14)-(17), and the results are shown in FIGS. 4 and 6, respectively. By comparing FIG. 3 with FIG. 4, and FIG. 5 with FIG. 6, it may be seen that using the dictionary and L1 minimization approach shown in the formulations (14)-(17) greatly improves sensitivity to T1, resolution of T1-T2 inversion and corresponding maps and reduces sensitivity of inversion to regularization $\lambda$.

Figure 7:
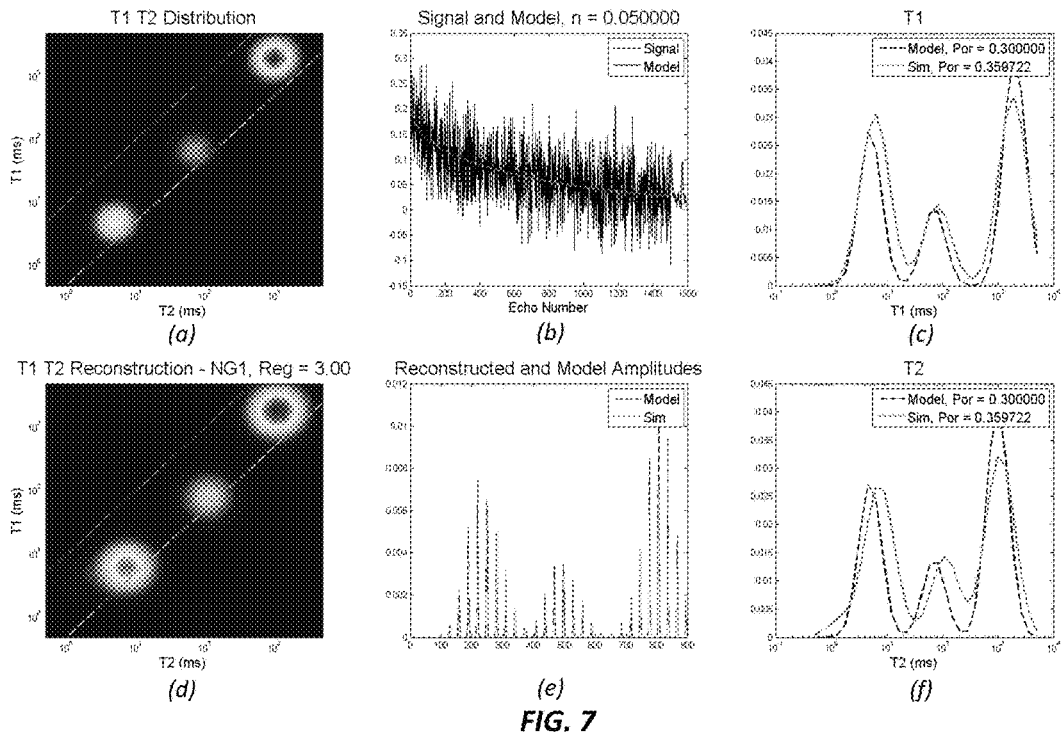
FIG. 7 is a set of graphs illustrating T1-T2 inversion results using an example least squares L1 norm minimization approach for a third example data set in accordance with an example embodiment.
Figure 8:
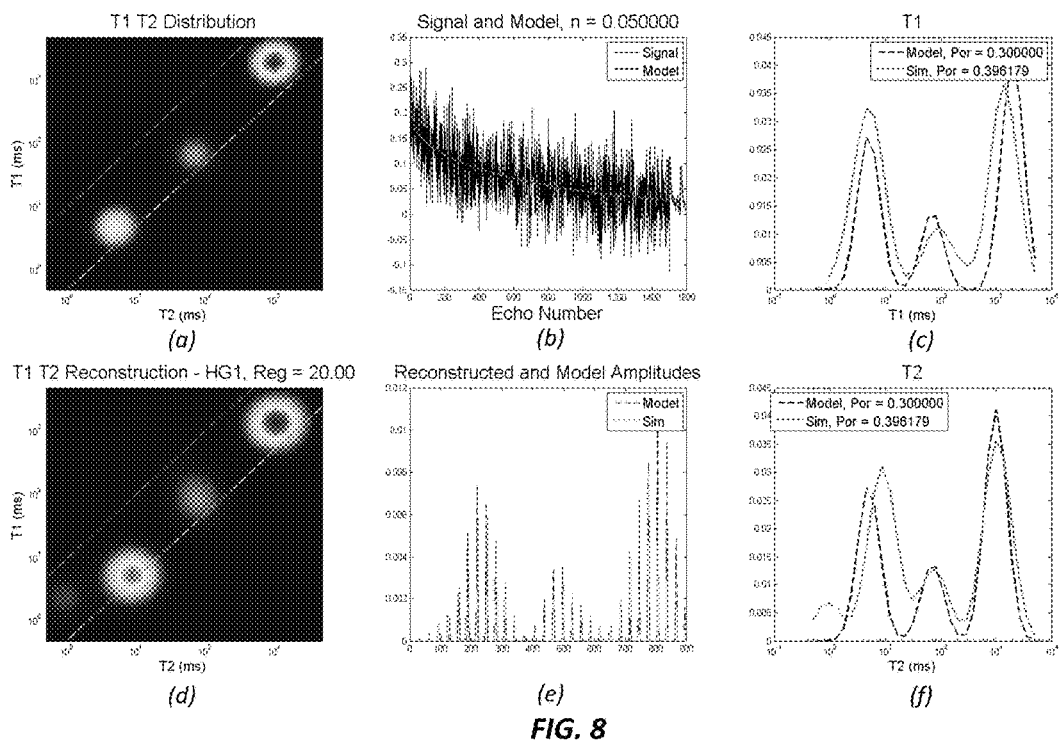
FIG. 8 is a set of graphs illustrating T1-T2 inversion results using an example Huber cost, a redundant dictionary of Gaussians and L1 norm minimization approach for the third example data set in accordance with an example embodiment.

In accordance with another example embodiment, different cost function formulations may also be used. For example, one such formulation uses Huber (e.g., L1 until a certain error is reached and then switching to L2) as a cost function in place of a simple L2 formulation, the results of which are shown in FIG. 8. By way of comparison, these results are similar with those obtained using the least square L1 penalty approach on the same example data set (i.e., the same approach used with the first and second examples shown in FIGS. 4 and 6), as seen in FIG. 7. In some implementations, using the Huber norm resulted in reduced sensitivity to noise in the measurements, whereas generally the L2 norm for the cost function may be relatively easier to code algorithmically, and may require somewhat less computational time, although either approach may be used in a given embodiment.

Accordingly, using the above-described L1 minimization approaches may advantageously allow resolving T1 components competitively with relatively few wait times (e.g., three). Further, adding just two more wait time may be sufficient to cover a complete T1 range, and provide resolution that any further addition of wait times will not markedly improve.

Figure 9:
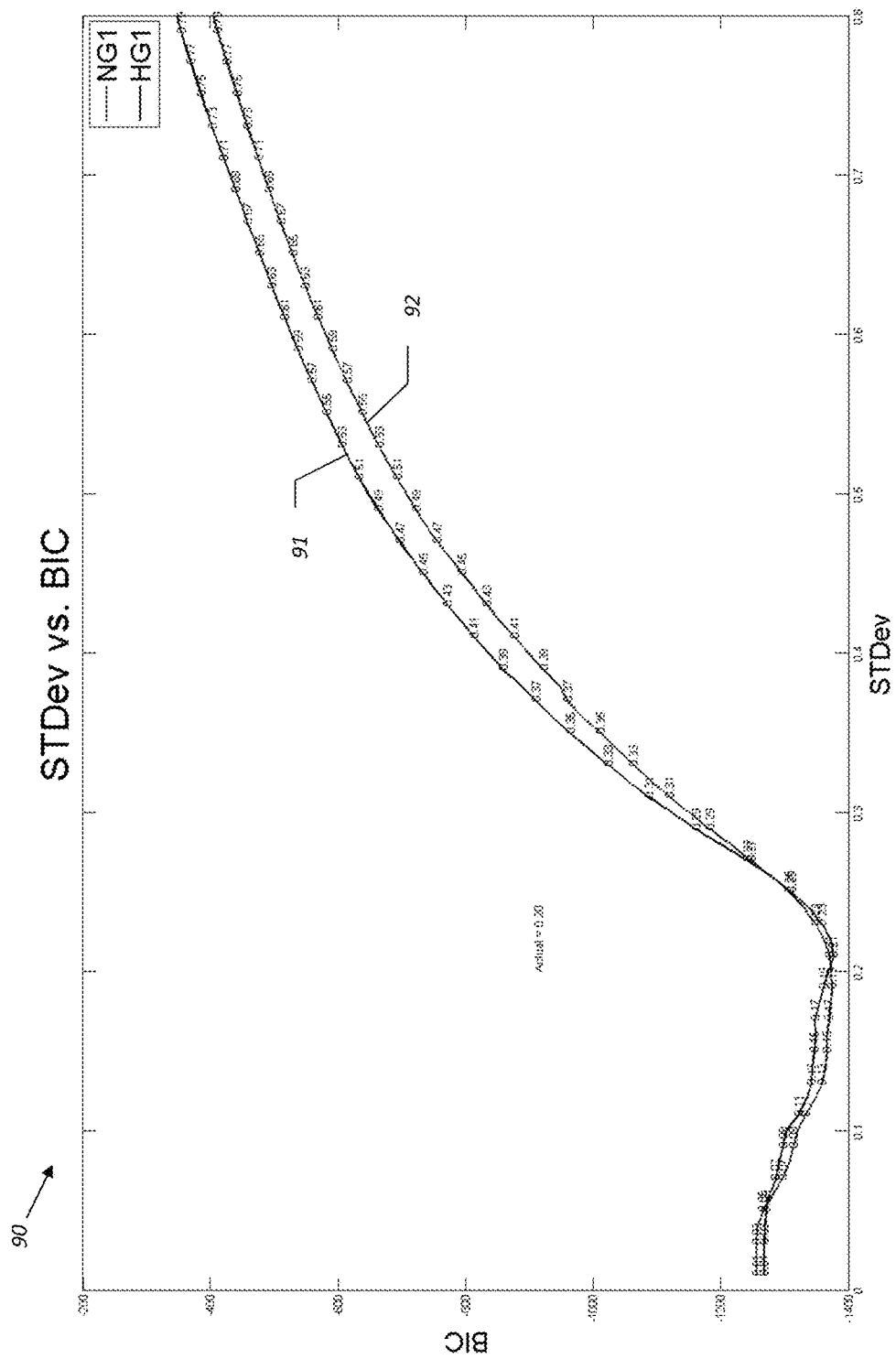
FIG. 9 is a graph of Bayesian Information Criteria (BIC) vs. a set of possible standard deviations for the Gaussian basis functions in the redundant Gaussians dictionary illustrating an example approach for pre-selecting a smaller size subset of optimal basis functions for use in the system and method of FIGS. 1 and 2, respectively.

Turning now to the graph 90 of FIG. 9, an example approach for determining desired standard deviations to be used to construct the basis function dictionary is now described. This approach reduces the overall size of the total available dictionary for NMR inversion. The approach uses an Akaike's Information Criteria (AIC)/Bayesian Information Criteria (BIC) type of information criteria against an extensive set of possible choices of standard deviations (i.e., the full dictionary of potential basis functions). In the illustrated example, the graph 90 of BIC vs. Gaussian dictionary standard deviation is for a case where a T1-T2 distribution was modeled using Gaussians of fixed width 0.2 and then inverted using a dictionary with specific standard deviation (as on the x axis) and L1 minimization of the penalty term with two different formulations of the cost function, Huber (HG1) and L2 (NG1), resulting in respective curves 91, 92. An inflexion or "elbow" may be observed near at 0.2, which is the region where the best results may generally be obtained. As such, this technique may be used to determine and restrict the choice of standard deviations in the creation of the dictionary of Gaussians (e.g., the subset of basis functions used for the dictionary may be taken from 0.1 to 0.3 standard deviations, and the remainder excluded). This technique will be particularly useful when the potential dictionary ends up being very large. It may be desirable to limit one degree of freedom of the basis functions in the dictionary to reduce the number of possible choices available, as will be appreciated by those skilled in the art.

In view of the foregoing, it will be understood that the above-described techniques may be extended to both lower single dimensional and higher three and more dimensional inversion of NMR or other types of measurement data. Moreover, the proposed approach for using a dictionary and L1 minimization may be used for various linear or non-linear inversions of the form as described in equation (1), such as volumetrics inversion, conductivity tensor inversion, acoustics slowness inversion, seismic inversion, geological structure inversion etc., with the selection of an appropriate dictionary.

With respect to the dictionary of basis functions, this may include known or best-considered basis functions using a priori knowledge or characteristics of solution space. I t may also include a standard set of basis functions such as Gaussians, wavelets, curvelets, Fourier, etc., which are generally considered to have desirable properties which are able to cover different solution spaces. The dictionary can also be a subset of known or observed but independent solutions out of which one is to be chosen. The basis functions may also be designed through adaptive techniques or machine learning using a training dataset of sufficient and/or randomly drawn number of acceptable solutions, as will be appreciated by those skilled in the art. Furthermore, the dimension or size of the dictionary may be managed by reducing the number of possible choices of free variables for each basis using the technique described above with respect to FIG. 9. This may be especially useful when there is a relatively large set of basis functions that could be used to cover a complete solution space.

Referring to the flow diagram 60 of FIG. 2, a method employing the above-described technique is now described. Beginning at Block 61, the method may include obtaining measured data for the geological formation based upon a logging tool (e.g., NMR, etc.), at Block 62, and generating a kernel describing a known linear mapping between the measured data and unknown data points representing at least one characteristic of the geological formation, and a redundant dictionary including a plurality of different basis functions expected to span the solution space of the unknown data points representing at least one characteristic of the geological formation (Block 63), as discussed further above. The method also illustratively includes determining the unknown data points representing the at least one characteristic of the geological formation from the measured data, the kernel and the redundant dictionary based upon an L1 minimization, at Block 64, as further discussed above, which concludes the method illustrated in FIG. 2 (Block 65).

Many modifications and other embodiments will come to the mind of one skilled in the art having the benefit of the teachings presented in the foregoing descriptions and the associated drawings. Therefore, it is understood that various modifications and embodiments are intended to be included within the scope of the appended claims.

That which is claimed is:

1. A method for analyzing at least one characteristic of a geological formation comprising:
    deploying a downhole logging tool in a wellbore traversing the geological formation;
    causing the downhole logging tool to make logging measurements of the geological formation while deployed in the wellbore;
    generating a kernel describing a known linear mapping between the logging measurements and unknown data points representing at least one characteristic of the geological formation;
    combining the kernel with a redundant dictionary including a plurality of different basis functions that span a solution space of the unknown data points thereby generating a transformed kernel that describes a linear mapping between the logging measurements and a sparse vector of corresponding amplitudes;
    processing an inversion using the logging measurements and the transformed kernel to compute the sparse vector of corresponding amplitudes, wherein the inversion is processed using an L1 minimization; and
    multiplying the plurality of different basis functions by the computed sparse vector of corresponding amplitudes to reconstruct the unknown data points representing the at least one characteristic of the geological formation.

2. The method of claim 1 wherein the plurality of different basis functions comprises a plurality of different Gaussian functions.

3. The method of claim 1 wherein the plurality of different basis functions comprises a plurality of different Fourier series, a plurality of different wavelet functions, or a plurality of different curvelets functions.

4. The method of claim 1 wherein the plurality of different basis functions are a subset of the known or observed but independent solutions.

5. The method of claim 1 wherein the plurality of different basis functions are derived using at least one of machine learning and adaptive learning.

6. The method of claim 1 wherein the downhole logging tool is a nuclear magnetic resonance (NMR) tool and the logging measurements are corresponding NMR measurements including NMR echoes acquired using a Carr-Purcell-Meiboom-Gill (CPMG) sequence.

7. The method of claim 6, wherein the basis functions comprise a plurality of different two-dimensional Guassians centered on corresponding allowed T1/T2 pairs in the unknown data points.

8. The method of claim 7, wherein the different Gaussians have different widths and the same heights.

9. The method of claim 1 wherein the at least one characteristic of the geological formation comprises porosity.

10. The method of claim 1 wherein the at least one characteristic of the geological formation comprises conductivity.

11. The method of claim 1 wherein the at least one characteristic of the geological formation comprises an acoustic characteristic.

12. The method of claim 1 wherein the at least one characteristic of the geological formation comprises a seismic characteristic.

13. The method of claim 1 wherein the at least one characteristic of the geological formation comprises geological structure inversion.

14. The method of claim 1 wherein the plurality of different basis functions comprises a subset of different basis functions within a standard deviation range of a dictionary of available basis functions.

15. The method of claim 1, wherein the sparse vector has a sparsity of less than about 1%.

16. An apparatus for analyzing at least one characteristic of a geological formation comprising:
    a downhole logging tool configured for deployment in a subterranean wellbore;
    a memory configured to record logging measurements made by the logging tool; and
    a processor configured to compute the at least one characteristic of the geological formation from the logging measurements via:
        generating a kernel describing a known linear mapping between the logging measurements and unknown data points representing at least one characteristic of the geological formation;
        combining the kernel with a redundant dictionary including a plurality of different basis functions that span a solution space of the unknown data points thereby generating a transformed kernel that describes a linear mapping between the logging measurements and a sparse vector of corresponding amplitudes;
        processing an inversion using the logging measurements and the transformed kernel to compute the sparse vector of corresponding amplitudes, wherein the inversion is processed using an L1 minimization; and
        multiplying the plurality of different basis functions by the computed sparse vector of corresponding amplitudes to reconstruct the unknown data points representing the at least one characteristic of the geological formation.

17. The apparatus of claim 16 wherein the plurality of different basis functions comprises a plurality of different Gaussian functions.

18. The apparatus of claim 16 wherein the plurality of different basis functions comprises a plurality of different Fourier series or a plurality of different wavelet functions.

19. The apparatus of claim 16 wherein the measured data comprises multi-dimensional nuclear magnetic resonance (NMR) data for the geological formation based upon an NMR tool.

20. A method for analyzing at least one characteristic of a geological formation comprising:
- deploying a nuclear magnetic resonance (NMR) logging tool in a wellbore traversing the geological formation;
- causing the NMR logging tool to make NMR measurements of the geological formation while deployed in the wellbore, wherein the NMR measurements include a plurality of echoes;
- generating a kernel describing a known linear mapping between the plurality of echoes and an unknown distribution of T1/T2 amplitudes representing at least one characteristic of the geological formation;
- combining the kernel with a redundant dictionary including a plurality of different Gaussian functions that span a solution space of the unknown data points thereby generating a transformed kernel that describes a linear mapping between the plurality of echoes and a sparse vector of corresponding amplitudes;
- processing an inversion using the plurality of echoes and the transformed kernel to compute the sparse vector of corresponding amplitudes, wherein the inversion is processed using an L1 minimization; and
- multiplying the plurality of different Gaussian functions by the computed sparse vector of corresponding amplitudes to reconstruct the unknown data points representing the at least one characteristic of the geological formation.

21. The method of claim 20, wherein the basis functions comprise a plurality of different two-dimensional Guassians centered on corresponding allowed T1/T2 pairs in the unknown data points.

22. The method of claim 21, wherein the different Gaussians have different widths and the same heights.

23. The method of claim 20, wherein the sparse vector has a sparsity of less than about 1%.

* * * * *